United States Patent [19]

Kezuka et al.

[11] Patent Number: 5,283,351

[45] Date of Patent: Feb. 1, 1994

[54] PROCESS FOR PRODUCING AN ORGANIC CARBONATE FROM AN ORGANIC HYDROXY COMPOUND AND CARBON MONOXIDE IN THE PRESENCE OF A PALLADIUM CATALYST

[75] Inventors: Hiroaki Kezuka, Tochigi; Fumio Okuda, Sodegaura, both of Japan

[73] Assignee: Idemitsu Kosan Co., Ltd., Tokyo, Japan

[21] Appl. No.: 859,930

[22] Filed: Mar. 30, 1992

[30] Foreign Application Priority Data

Apr. 11, 1991 [JP] Japan .................. 3-079036

[51] Int. Cl.$^5$ .............. C07C 69/96; C07C 68/00; C07C 69/88
[52] U.S. Cl. ............. 558/260; 558/265; 558/268; 558/270; 558/274; 558/275; 558/277
[58] Field of Search .......... 558/260, 265, 268, 270, 558/274, 277, 275

[56] References Cited

U.S. PATENT DOCUMENTS

| | | | |
|---|---|---|---|
| 3,114,762 | 12/1963 | Mador et al. | 558/260 X |
| 4,096,168 | 6/1978 | Hallgren | 558/268 |
| 4,096,169 | 6/1978 | Chalk | 558/268 |
| 4,201,721 | 5/1980 | Hallgren | 560/204 |
| 4,281,174 | 7/1981 | Current | 558/260 X |
| 4,349,485 | 9/1982 | Hallgren | 558/260 X |
| 4,361,519 | 11/1982 | Hallgren | 558/277 |
| 4,785,130 | 11/1988 | Bhattacharya | 558/277 |
| 5,118,818 | 6/1992 | Delledonne et al. | 558/260 X |
| 5,120,524 | 6/1992 | Ellgen | 558/260 X |
| 5,132,447 | 7/1992 | King | 558/260 X |

FOREIGN PATENT DOCUMENTS

| | | |
|---|---|---|
| 0350697 | 1/1990 | European Pat. Off. ........ 558/268 |
| 0350700 | 1/1990 | European Pat. Off. ........ 558/268 |
| 0366177 | 5/1990 | European Pat. Off. ........ 558/277 |
| 0425197 | 5/1991 | European Pat. Off. ........ 528/277 |
| 45-11129 | 4/1970 | Japan ........ 558/260 |
| 53-68747 | 6/1978 | Japan ........ 558/260 |
| 54-135743 | 10/1979 | Japan ........ 558/260 |
| 55-102539 | 5/1980 | Japan ........ 558/260 |
| 55-94338 | 7/1980 | Japan ........ 558/260 |
| 56-38143 | 9/1981 | Japan ........ 558/260 |
| 56-38144 | 9/1981 | Japan ........ 558/260 |
| 56-38145 | 9/1981 | Japan ........ 558/260 |
| 62-126152 | 6/1987 | Japan ........ 558/260 |
| 62-212305 | 9/1987 | Japan ........ 558/260 |
| 1-165551 | 6/1989 | Japan ........ 558/260 |
| 2-104564 | 4/1990 | Japan ........ 558/260 |
| 2-142754 | 5/1990 | Japan ........ 558/260 |

OTHER PUBLICATIONS

Grazianz et al, J. Organometallic Chem. vol. 27, pp. 275–278 (1971).

*Primary Examiner*—Floyd D. Higel
*Attorney, Agent, or Firm*—Frishauf, Holtz, Goodman & Woodward

[57] ABSTRACT

A process for efficiently producing an organic carbonate which comprises reacting an organic hydroxy compound and carbon monoxide in the absence of oxygen and in the presence of a catalyst comprising (a) palladium or a palladium compound, (b) a quinone or an aromatic diol formed by reduction of the quinone or a mixture thereof, and (c) a halogenated onium compound is disclosed.

17 Claims, No Drawings

PROCESS FOR PRODUCING AN ORGANIC CARBONATE FROM AN ORGANIC HYDROXY COMPOUND AND CARBON MONOXIDE IN THE PRESENCE OF A PALLADIUM CATALYST

BACKGROUND OF THE INVENTION

1. Field of the Invention

The present invention relates to a process for producing an organic carbonate. More particularly, the present invention is concerned with a process for producing an organic carbonate efficiently from an organic hydroxy compound using a specified catalyst in the absence of oxygen.

2. Description of the Related Arts

Heretofore, in order to produce organic carbonates, various processes have been proposed. For example, as the process for producing aromatic organic carbonates, a process using alkali metals and alkaline earth metals, basic quaternary ammonium, quaternary phosphonium or tertiary sulfonium compounds, hydroxides of alkali metals or alkaline earth metals, salts of strong bases and weak organic acids, bases such as primary amines, secondary amines, tertiary amines, and palladium (Japanese Patent Publication No. 38143/1981) as the catalyst; a process using a catalyst comprising Pd and the base as mentioned above, an oxidizing agent (compounds of group IIIA, IVA, VA, VIA, IB, IIB, VIB, VIIB metals) (Japanese Patent Publication No. 38144/1981), a process using a catalyst comprising Pd and a base, oxidizing agent (Co, Mn) and a drying agent (Japanese Patent Publication No. 38145/1981); a process using a base and a VIII group metal in oxidized state of +1 (Ru, Rh, Pd, Os, Ir, Pt) as a catalyst (Japanese Patent Application Laid-Open No. 68747/1978); a process using a base and VIII metal as the catalyst in an anhydrous condition (Specification of U.S. Pat. No. 4,201,721); a process using a catalyst comprising a base and VIII metal, and an oxidizing agent (having a higher oxidization potential than VIII metal (Japanese Patent Application Laid-Open No. 135743/1979); a process using a catalyst comprising Pd and a base, oxidizing agent, phase-transfer agent and a drying agent (Japanese Patent Application Laid-Open No. 102539/1980); a process using a catalyst comprising a base and a VIII group metal, and an oxidizing agent (Specification of U.S. Pat. No. 4,349,485); a process using a catalyst comprising Pd, Mn, $R_4N^+X^-$ (R indicates an alkyl group and X indicates a halogen) and quinone (Japanese Patent Application Laid-Open No. 104564/1990); a process using a catalyst comprising Pd, Co, $R_4N^+X^-$ (R and X are as defined above) and quinone (Japanese Patent Application Laid-Open No. 142754/1990); a process using a catalyst comprising Pd, an alkali metal or an alkaline earth metal or onium iodide compound and zeolites (Japanese Patent Application Laid-Open No. 165551/1989) are mentioned. However, the above-mentioned processes for producing aromatic organic carbonates have a problem in that the yield was insufficient.

As the process for producing aliphatic organic carbonates, a process using Pd, Cu or Fe as the catalyst (Specification of U.S. Pat. No. 3,114,762); a process for producing divalent Cu ion (Japanese Patent Publication No. 11129/1970) are mentioned. These processes, however, have problems in that the rate of the catalytic reaction is low, and that a large amount of the catalyst is required. Further, according to these processes, the yield is insufficient.

On the other hand, as the carbonylation method using Pd component and quinone component, a process for producing oxalic diester using $Pd(NO_3)_2$ and quinones as the catalyst (Japanese Patent Application Laid-Open No. 94338/1980); a process for producing oxalic diester using Pd, quinone and a redox agent (U.S. Pat. No. 4281174), a process for producing cinnamic acid ester using Pd, quinone and a redox agent (Japanese Patent Application Laid-Open No. 126152/1987); a process for producing dialkyl carbonate using Pt group, Cu and quinone (Japanese Patent Application Laid-Open No. 212305/1987) are mentioned. However, these carbonylation methods have many problems in that the kinds of the products to be produced are limited and that the yield of the desired product is not sufficient.

SUMMARY OF THE INVENTION

The present inventors have intensively studied to overcome the above problems in prior arts and to establish a process for producing efficiently an organic carbonate from an organic hydroxy compound.

As the result, it was found that the above object can be attained by performing a reaction in the absence of oxygen using a catalyst comprising (a) palladium or a palladium compound, (b) a quinone, an aromatic diol formed by reduction of the quinone, or a mixture thereof, and (c) a halogenated onium compound. The present invention was accomplished based on such findings.

An object of the present invention is to provide an improved process for producing an organic carbonate which can be used as the starting material for various chemical products.

Another object of the present invention is to provide a process for producing various kinds of organic carbonates.

Still another object of the present invention is to provide a process for efficiently producing an organic carbonate with a small amount of catalyst.

The present invention provides a process for producing an organic carbonate which comprises reacting an organic hydroxy compound and carbon monoxide in the absence of oxygen by using a catalyst comprising (a) palladium or a palladium compound, (b) a quinone, an aromatic diol formed by reduction of the quinone, or a mixture thereof, and (c) a halogenated onium compound.

DESCRIPTION OF PREFERRED EMBODIMENTS

The organic hydroxy compounds to be used in the process of the present invention vary depending on the kinds of the organic carbonate to be produced. For example, aliphatic monohydroxy or aliphatic polyhydroxy compounds having 1 to 6 carbon atoms, cycloaliphatic monohydoxy or cycloaliphatic polyhydroxy compounds having 3 to 15 carbon atoms, and aromatic monohydroxy or aromatic polyhydroxy compounds having 6 to 15 carbon atoms are mentioned. Aliphatic monohydroxy compounds include alcohols such as methanol, ethanol, propanol, butanol, pentanol, and hexanol; aliphatic polyhydroxy compounds include glycols (dihydroxy compounds) such as ethylene glycol, propylene glycol, 1,4-butanediol, 1,5-pentanediol, and 1,6-hexanediol and trihydroxy compounds such as glycerol. Cycloaliphatic monohydroxy compounds include cyclic alcohols such as cyclopentanol, cyclohexanol and cycloheptanol; cycloaliphatic polyhydroxy compounds include alicyclic diols such as cyclopentandiols, and cyclohexanediols. Aromatic monohydroxy compounds include phenolic compounds such as phenol, cresols, naphthols, p-methylphenol, and t-butylphenol (e.g. p-t-butylphenol); and aromatic polyhydroxy compounds include aromatic dihydroxy compounds such as phenolic compounds for example catechol, hydroquinone, resorcinol, and 2,2-bis(4-hydroxyphenyl)-propane (bisphenol A). If these phenolic compounds have an alkyl group or alkyl groups as a substituent, the alkyl group having 1 to 6 carbon atoms, preferably 1 to 4 carbon atoms is preferred.

Carbon monoxide to be reacted with the above-mentioned organic hydroxy compounds may be diluted with inert gas, or mixed with hydrogen, as long as it is not contaminated by oxygen.

The catalyst to be used in the process of the present invention comprises components (a), (b) and (c), as described above. Herein, with regard to the palladium compounds as component (a), for example, palladium chloride ($PdCl_2$), palladium bromide ($PdBr_2$), palladium iodide ($PdI_2$), palladium acetate ($Pd(OAc)_2$; Ac indicates an acetyl group), palladium nitrate ($Pd(NO_3)_2$), palladium sulfate ($PdSO_4$), and dichlorobis(triphenylphosphine)palladium ($PdCl_2(PPh_3)_2$) are mentioned. As palladium catalysts of deposited type, Pd/active carbon, Pd/alumina, Pd/silica, Pd/silica .alumina, Pd/zeolite and the like are mentioned.

A quinone, an aromatic diol formed by reduction of the quinone, or mixtures thereof as component (b) includes various ones. For example, a quinone includes benzoquinone, 1,2-benzoquinone, 1,4-naphthoquinone, anthraquinone, and 1,4-phenanthrenequinone. An aromatic diol includes one formed by reduction of benzoquinone, 1,2-benzoquinone, 1,4-naphthoquinone, anthraquinone or 1,4-phenanthrenequinone, such as hydroquinone, catechol, 1,4-dihydroxynaphthalene, 9,10-dihydroxyanthracene, and 1,4-dihydroxyphenanthrene.

With regard to halogenated onium compounds as component (c), tetraalkylammonium halide (specifically, $Pr_4NCl$, $Bu_4NCl$, $Pr_4NBr$, $Bu_4NBr$, $Pr_4NI$, and $Bu_4NI$), tetraalkylphosphonium halide (specifically, $Pr_4PCl$, $Bu_4PCl$, $Pr_4PBr$, $Bu_4PBr$, $Pr_4PI$, and $Bu_4PI$), trialkylsulfonium halide (specifically, $Pr_3SCl$, $Bu_3SCl$, $Pr_3SBr$, $Bu_3SBr$, $Pr_3SI$, and $Bu_3SI$) are mentioned. Herein, Pr indicates a propyl group, and Bu indicates a butyl group.

The amount of the catalyst to be used in the process of the present invention is not limited particularly, but it is usually determined in the range of catalytic amounts. However, component (a) should be $10^{-5}$ to 1 mol, preferably $10^{-4}$ to $10^{-2}$ mol as Pd based on 1 mol of organic hydroxy compound for the starting material. If it is less than $10^{-5}$ mol, the reaction rate becomes impractically low. If it exceeds 1 mol, an effect corresponding to the amount is not obtained, which is economically disadvantageous. The amount of Component (b) is preferably at least 0.5 equivalent to the organic hydroxy compound. If it is less than 0.5 equivalent, the reaction sometimes does not proceed sufficiently. Component (c) is usually 1 to 100 mol, preferably 1 to 50 mol, based on 1 mol of Pd as component (a).

The process of the present invention proceeds also in the absence of solvent, but preferably it proceeds in the presence of solvent. As the solvents to be used there, for example, aliphatic hydrocarbons, cycloaliphatic hydrocarbons, aromatic hydrocarbons, halogenated hydrocarbons, ethers and esters are mentioned. Specific examples of the aliphatic hydrocarbons, cycloaliphatic hydrocarbons and aromatic hydrocarbons are hexane, heptane, cyclohexane, benzene, toluene, xylenes and the like; and specific examples of halogenated hydrocarbons are methylene chloride, chloroform, chlorobenzene and the like; and specific examples of ethers are dioxanes, anisole, diphenyl ether and the like; and specific examples of esters are methyl acetate, ethyl acetate, phenyl acetate, methyl propionate, ethyl propinonate and the like.

The reaction temperature is not limited particularly, but is usually 50° to 200° C., and preferably 70° to 150° C. At too high a temperature, side reactions such as a decomposition reaction undesirably occur, while at a low temperature, the reaction rate becomes impractically low. The reaction pressure can be selected properly depending on the circumstances, but is preferably at least 30 kg/cm² when an aromatic hydroxy compound is used as the starting material, and preferably at least 1 kg/cm² when an aliphatic hydroxy compound is used as the starting material.

The reaction system may be any of a batch system, semi-continuous and continuous system. Herein, the state in the reaction system is a liquid phase or a mixed state of a liquid phase and a vapor phase. The state of the catalyst in the reaction system may be homogeneous or heterogeneous, and solvents and catalysts may be selected appropriately. The above-mentioned components of the material and catalyst can be diluted if necessary, and as the diluents for them, inert solvents such as saturated hydrocarbons are used in the liquid phase, and inert gases such as nitrogen, ethane, and propane are used in the vapor phase.

In the process of the present invention, the organic hydroxy compound described above and carbon monoxide are reacted in the absence of oxygen and in the presence of the above catalyst to produce an organic carbonate. The objective organic carbonate to be obtained in the reaction (that is, carbonate of organic hydroxy compound) includes various ones. For example, when an organic hydroxy compound represented by the general formula: R—OH (R is an alkyl group having 1 to 6 carbon atoms including methyl, ethyl, propyl, butyl, pentyl, and hexyl group, or an aryl group having 6 to 15 carbon atoms including phenyl, methylnaphthyl, naphthyl, and butylphenyl group) is used, an organic carbonate represented by the general formula:

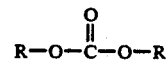

(R is as defined above) can be obtained. Specific examples of said organic compounds are dimethyl carbonate, diethyl carbonate, and diphenyl carbonate.

When an organic hydroxy compounds represented by the general formula: HO—$R^1$—OH ($R^1$ is an alkylene having 1 to 6 carbon atoms including ethylene, propylene, butylene, pentylene, and hexylene; or a divalent group which results by removing 2 hydroxy groups from the above-mentioned aromatic dihydroxy compounds, including: phenylene, methylphenylene, and

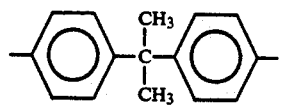

is used, an organic carbonate represented by the general formula:

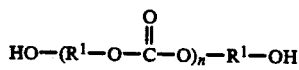

(R is as defined above, and n is an integer of at least 1) can be obtained.

The by-products are dimethyl oxalate and salicylate of organic hydroxy compounds. Specific examples of these by-products are dimethyl oxalate, diethyl oxalate and phenyl salicylate. The objective product and the by-product can be separated by a conventional method such as extraction.

As described above, according to the process of the present invention, organic carbonates used as an intermediate material useful in chemical industry can be produced efficiently.

Consequently, the present invention is practically highly advantageous in the field of chemical industry, as a process for efficiently producing an organic carbonate which can be used as the starting material for intermediate materials of various chemical products including the intermediates for producing polycarbonate (such as aryl carbonate) and the intermediates of pharmaceuticals or agricultural chemicals (such as alkyl carbonate), or solvents.

The present invention will be described in greater detail with reference to examples and comparative examples as follows, provided that the present invention is not limited thereto.

EXAMPLE 1

In a 200 ml autoclave, 9.41 g (100 mmol) of phenol, 67.4 mg (0.3 mmol) of palladium acetate, 0.973 g (9 mmol) of benzoquinone, 1.451 g (4.5 mmol) of tetrabutylammonium bromide, and 50 ml of methylene chloride were sealed.

The air in said autoclave was replaced with nitrogen by pressurizing and depressuring with nitrogen, and further, replaced with carbon monoxide by pressurizing and depressuring with the carbon monoxide. Then, the carbon monoxide was pressurized so that the pressure is 60 kg/cm$^2$G at 25° C., then heated to 100° C., and reacted for 3 hours. After cooled and depressurized, and the gas and the reaction solution in the autoclave were analyzed by gas chromatography. As the result, 2.9 mmol of diphenyl carbonate and 0.9 mmol of carbon dioxide were produced. Accordingly, the selectivity of carbon monoxide to diphenyl carbonate was 76.3%.

EXAMPLE 2

The same reaction as in Example 1 was repeated except that dichlorobis(triphenylphosphine)palladium (PdCl$_2$(PPh$_3$)$_2$)(Ph indicates a phenyl group) was used in place of palladium acetate. As the result of analyzing the gas and the reaction solution in the autoclave by gas chromatography, 3.0 mmol of diphenyl carbonate and 2.4 mmol of carbon dioxide were produced. Accordingly, the selectivity of carbon monoxide to diphenyl carbonate was 55.6%.

EXAMPLE 3

The same reaction as in Example 1 was repeated except that tetrabutylphosphonium bromide ((C$_4$H$_9$)$_4$PBr) was used in place of tetrabutylammonium bromide. As the result of analyzing the gas and the reaction solution in the autoclave by gas chromatography, 2.9 mmol of diphenyl carbonate and 3.1 mmol of carbon dioxide were produced. Accordingly, the selectivity of carbon monoxide to diphenyl carbonate was 48.3%.

EXAMPLE 4

The same reaction as in Example 1 was repeated except that methanol was used in place of phenol. As the result of analyzing the gas and the reaction solution in the autoclave by gas chromatography, 4.5 mmol of dimethyl carbonate and 0.5 mmol of carbon dioxide were produced. Accordingly, the selectivity of carbon monoxide to dimethyl carbonate was 90.0%.

COMPARATIVE EXAMPLE 1

The same reaction as in Example 1 was repeated except that a mixed gas of 95% by volume of carbon monoxide and 5% by volume of oxygen was pressurized in with 60 kg/cm$^2$G. As the result of analyzing the gas and the reaction solution in the autoclave by gas chromatography, 3.5 mmol of diphenyl carbonate and 18.0 mmol of carbon dioxide were produced. Accordingly, the selectivity of carbon monoxide to diphenyl carbonate was 16.3%.

COMPARATIVE EXAMPLE 2

The same reaction as in Comparative Example 1 was repeated except that 0.224 g (0.9 mmol) of tetrahydrate of cobalt acetate was further sealed in. As the result of analyzing the gas and the solution in the autoclave, 4.7 mmol of diphenyl carbonate and 89.2 mmol of carbon dioxide were produced. Accordingly, the selectivity of carbon monoxide to diphenyl carbonate was 5.0%.

COMPARATIVE EXAMPLE 3

The same reaction as in Example 1 was repeated except that 0.115 g (0.3 mmol) of dichlorobis(benzonitrile)palladium (PdCl$_2$(PhCN)$_2$) in place of palladium acetate and 0.582 g (4.5 mmol) of N-ethyldiisopropylamine in place of tetrabutylammonium bromide were used. As the result of analyzing the gas and the solution in the autoclave by gas chromatography, production of diphenyl carbonate was not confirmed.

COMPARATIVE EXAMPLE 4

The same reaction as in Example 1 was repeated except that 0.080 g (0.3 mmol) of PdBr$_2$, 0.335 (1.5 mmol) of CuBr$_2$, 0.071 g (0.6 mmol) of KBr, and 0.177 g (1.8 mmol) of CH$_3$COOK were added, and that 0.130 g (1.2 mmol) of benzoquinone was added. As the result of analyzing the gas and the solution in the autoclave, production of diphenyl carbonate was not confirmed.

We claim:

1. A process for producing an organic carbonate which comprises reacting an organic hydroxy compound and carbon monoxide in the absence of oxygen and in the presence of a catalyst consisting essentially of (a) palladium or a palladium compound, (b) one or more compounds selected from the group consisting of a quinone and an aromatic diol formed by reduction of a quinone, and (c) an onium halide compound.

2. The process according to claim 1, wherein the organic hydroxy compound is one or more compounds selected from the group consisting of an aliphatic monohydroxy compound having 1 to 6 carbon atoms, an aliphatic polyhydroxy compound having 1 to 6 carbon atoms, a cycloaliphatic monohydroxy compound having 3 to 15 atoms, a cycloaliphatic polyhydroxy compound having 3 to 15 carbon atoms, an aromatic monohydroxy compound having 6 to 15 carbon atoms, and an aromatic polyhydroxy compound having 6 to 15 carbon atoms.

3. The process according to claim 1, wherein the organic hydroxy compound is an aromatic monohydroxy compound having 6 to 15 carbon atoms or an aromatic polyhydroxy compound having 6 to 15 carbon atoms.

4. The process according to claim 3, wherein the organic hydroxy compound is phenol, cresol, naphthol, p-methylphenol, or t-butylphenols.

5. The process according to claim 3, wherein the organic hydroxy compound is catechol, hydroquinone, resorcinol or bisphenol A.

6. The process according to claim 1, wherein said (a) is palladium chloride, palladium bromide, palladium iodide, palladium acetate, palladium nitrate, or palladium sulfate.

7. The process according to claim 1, wherein said (a) is palladium which is deposited on active carbon, alumina, silica, silica-alumina, or zeolite.

8. The process according to claim 1, wherein said (b) is benzoquinone, 1,2-benzoquinone, 1,4-naphthoquinone, anthraquinone, or 1,4-phenanthrenequinone.

9. The process according to claim 1, wherein said (b) is hydroquinone, catechol, 1,4-dihydroxynaphthalene, 9,10-dihydroxyanthracene, or 1,4-dihydroxyphenanthrene.

10. The process according to claim 1, wherein the onium halide compound is a tetraalkylammonium halide, a tetraalkylphosphonium halide, or a trialkylsulfonium halide.

11. The process according to claim 10, wherein the onium halide compound is $(C_3H_7)_4NCl$, $(C_4H_9)_4NCl$, $(C_3H_7)_4NBr$, $(C_4H_9)NBr$, $(C_3H_7)_4NI$, or $(C_4H_9)_4NI$.

12. The process according to claim 10, wherein the onium halide compound is $(C_3H_7)_4PCl$, $(C_4H_9)_4PCl$, $(C_3H_7)_4PBr$, $(C_4H_9)_4PBr$, $(C_3H_7)_4PI$, or $(C_4H_9)_4PI$.

13. The process according to claim 10, wherein the onium halide compound is $(C_3H_7)_3SCl$, $(C_4H_9)_3SCl$, $(C_3H_7)_3SBr$, $(C_4H_9)_3SBr$, $(C_3H_7)_3SI$, or $(C_4H_9)_3SI$.

14. The process according to claim 1, wherein the organic hydroxy compound is an aromatic hydroxy compound, the reaction is carried out at a reaction temperature of 50° to 200° C., and at a reaction pressure of at least 30 kg/cm$^2$.

15. The process according to claim 1, wherein the organic hydroxy compound is an aliphatic hydroxy compound, the reaction is carried out at a reaction temperature of 50° to 200° C., and at a reaction pressure of at least 1 kg/cm$^2$.

16. The process according to claim 1, wherein the organic hydroxy compound is selected from the group consisting of methanol, ethanol, propanol, butanol, pentanol, hexanol, ethylene glycol, propylene glycol, 1,4-butanediol, 1,5-pentanediol, 1,6-hexanediol, glycerol, cyclopentanol, cyclohexanol, cycloheptanol, cyclopentanediol, cyclohexanediol, phenol, cresol, naphthol, p-methylphenol, t-butylphenol, catechol, hydroquinone, resorcinol and 2,2-bis(4-hydroxy phenol)-propane; the catalyst comprises (a) palladium, palladium chloride, palladium bromide, palladium iodide, palladium acetate, palladium nitrate, palladium sulfate or dichlorobis(triphenylphosphine) palladium, (b) quinone, benzoquinone, 1,2-benzoquinone, 1,4-naphthoquinone, anthraquinone, 1,4-phenanthrequinone or an aromatic diol formed by reduction of benzoquinone, 1,2-benzoquinone, 1,4-naphtroquinone, anthaquinone or 1,4-phenanthrenequinone and (c) a onium halide compound selected from the group consisting of $(C_3H_7)_4NCl$, $(C_4H_9)_4NCl$, $(C_3H_7)_4NBr$, $(C_4H_9)_4NBr$, $(C_3H_7)_4NI$, $(C_4H_9)_4NI$, $(C_3H_7)_4PCl$, $(C_4H_9)_4PCl$, $(C_3H_7)_4PCl$, $(C_4H_9)_4PBr$, $(C_3H_7)_4PI$, $(C_4H_9)_4PI$, $(C_3H_7)_3SCl$, $(C_4H_9)_3SCl$, $(C_4H_9)_3SBr$, $(C_3H_7)_3SI$ and $(C_4H_9)SI$; said (a) is in an amount of $10^{-5}$ mol to 1 mol based on Pd per 1 mol of the organic hydroxy compound; said (b) is in an amount of at least 0.5 equivalents of the organic hydroxy compound; said (c) is 1 to 100 mol based on 1 mol of Pd as said (a); the process is carried out at a temperature of 50° to 200° C. and at a pressure of at least 1 kg/cm$^3$.

17. The process according to claim 16, wherein said (a) is in an amount of $10^{-4}$ to $10^{-2}$ mol based on Pd per 1 mol of the organic hydroxy compound; said (c) is 1 to 50 mol based on 1 mol of Pd as said (a); said temperature is 70° to 150° C. and said pressure is at least 1 kg/cm$^2$.

* * * * *